United States Patent [19]

Broadley

[11] Patent Number: 5,147,524
[45] Date of Patent: Sep. 15, 1992

[54] PH SENSOR

[75] Inventor: Scott T. Broadley, Mission Viejo, Calif.

[73] Assignee: Broadley-James Corporation, Santa Ana, Calif.

[21] Appl. No.: 735,993

[22] Filed: Jul. 25, 1991

[51] Int. Cl.⁵ .......................................... G01N 27/26
[52] U.S. Cl. .................................. 204/433; 204/435; 204/420; 204/153.21
[58] Field of Search ............ 204/420, 433, 435, 153.21

[56] References Cited

U.S. PATENT DOCUMENTS

| | | | |
|---|---|---|---|
| 3,264,205 | 8/1966 | Leonard et al. | 204/435 |
| 3,281,348 | 10/1966 | Schumacher et al. | 204/435 |
| 3,440,525 | 4/1969 | Cardeiro | 204/433 |
| 3,666,652 | 5/1972 | Krauer et al. | 204/409 |
| 4,112,352 | 9/1978 | Barben, II | 204/433 |
| 4,128,468 | 12/1978 | Bukamier | 204/433 |
| 4,235,688 | 11/1980 | Sudrabin et al. | 204/435 |

Primary Examiner—John Niebling
Assistant Examiner—Bruce F. Bell
Attorney, Agent, or Firm—Knobbe, Martens, Olson & Bear

[57] ABSTRACT

A pH sensor includes a unitary cylindrical semi-porous plug which is formed with a central bore and is also formed with a cavity near a first end of the plug. A pH electrode is positioned in the central bore and extends outwardly from the second end of the plug for contacting a specimen fluid, and a reference electrode is positioned in the cavity. The plug is saturated with an electrolyte to establish electrochemical conductivity between the reference electrode and specimen fluid. To prevent ions from the specimen fluid from migrating through the plug and contaminating the reference electrode, a plurality of notches are radially machined part way through the plug and filled with ion-impermeable epoxy. The notches are preferably oriented at oblique angles relative to the axis of the plug to form "dead end" ion traps that will immobilize and impede a substantial proportion of contaminating ions, thus prolonging the life of the electrode.

19 Claims, 1 Drawing Sheet

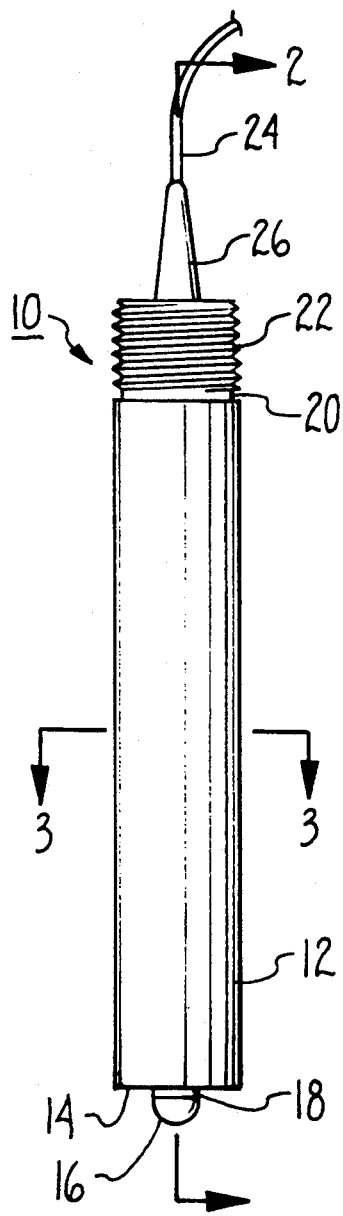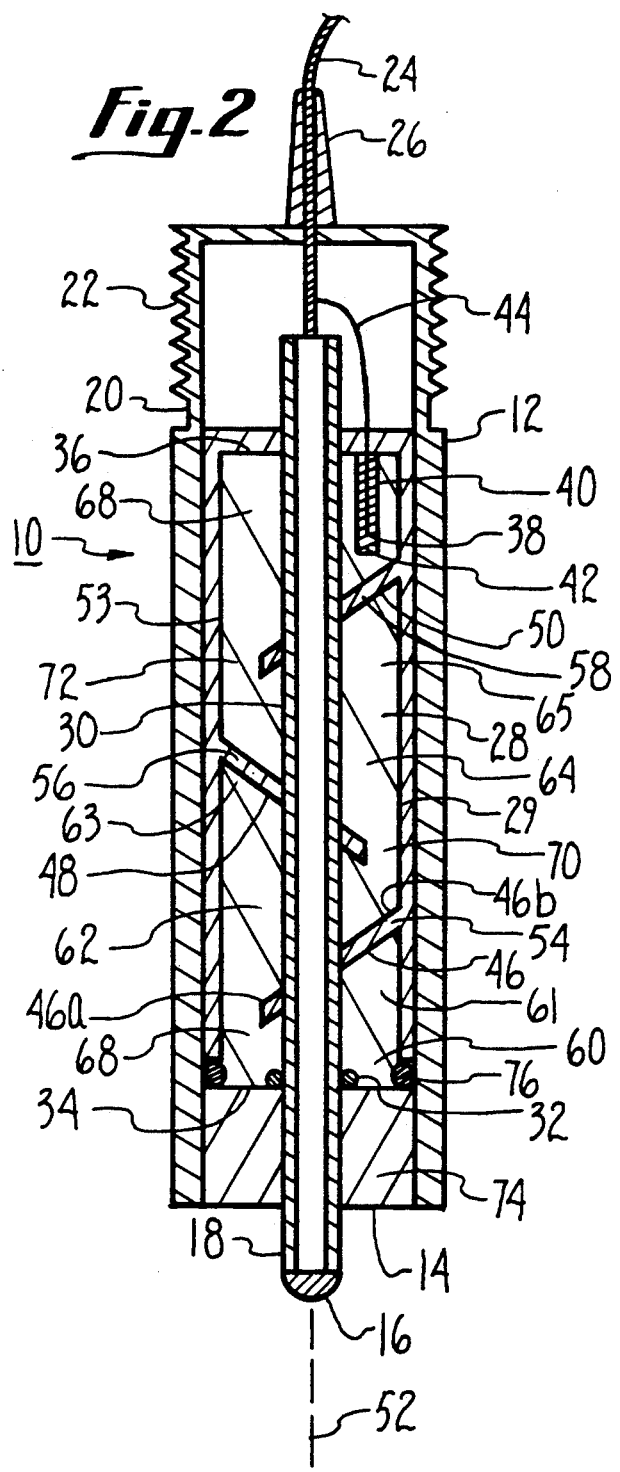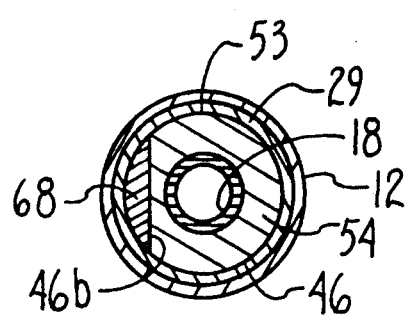

PH SENSOR

FIELD OF THE INVENTION

The present invention relates to instruments for sensing the characteristics of a fluid. More particularly, the present invention relates to pH sensors. The present invention particularly, though not exclusively, relates to reference cells for pH sensors.

BACKGROUND

Devices familiarly referred to as pH electrode sensors are widely used to sense the acidity of (i.e., hydrogen ion concentration in) many types of fluids. Typically, a pH sensor consists of two electrodes, a pH electrode and a reference electrode, which are together connected to an instrument that senses the difference in the electrical potential between the electrodes. Ordinarily, the reference electrode is located in the sensor coaxially within a chamber coaxially surrounding the pH electrode, and a reference solution having a known electrolyte concentration surrounds the reference electrode. See, for example, U.S. Pat. No. 3,741,884.

To measure the pH of a specimen fluid, the sensor structure, including the pH electrode and reference electrode, is immersed in the fluid, with the pH electrode in direct contact with the fluid. The reference electrode, on the other hand, is in electrochemical communication with the specimen fluid through a salt bridge. In accordance with well-known electrochemical principles, the reference electrode generates a stable potential, regardless of the pH of the specimen fluid. The pH electrode, on the other hand, generates a potential that varies as a function of the pH. The potential difference between the electrodes is measured and is instrumentally correlated to pH.

The stability of the reference electrode's potential is critical. If that potential changes over time, or if it changes in response to pH, an accurate pH reading will not be obtained.

To establish an electrical contact between the reference electrode and the specimen fluid, the chamber that holds the reference electrode is typically surrounded by a semi-porous material which is impregnated with a salt, e.g., potassium chloride. The effect of the salt is to electrically "bridge" the space between the specimen fluid and reference electrode.

Not surprisingly, many structures have been introduced which provide for electrochemical contact between the reference solution and the specimen fluid by means of a "salt bridge". For example, U.S. Pat. No. 3,440,525 to Cardeiro discloses a salt bridge comprising a porous plug of wood saturated with electrolyte. One end of the plug contacts the specimen liquid, and the other is in the electrolyte solution surrounding the reference electrode. Numerous pathways exist through the many capillaries in the wood so that the salt bridge solution can make electrochemical contact with the specimen fluid. Thus, if some of the capillaries become clogged, electrochemical contact between the reference solution and specimen fluid can still be maintained through other of the capillaries.

Unfortunately, the many capillaries of the Cardeiro plug establish the possibility of a substantial flow of contaminating ions through the plug. Because the osmotic pressure differential between the specimen fluid (which typically has a low osmolality) and the electrolyte solution, the specimen fluid will attempt to migrate into the salt bridge and into the electrolyte solution. Contaminating ions can reach the electrolyte solution and the reference electrode, causing changes in the reference potential and corresponding errors or instability in pH measurement.

To overcome the problems associated with the Cardeiro plug, U.S. Pat. No. 4,112,352, which issued to Barben, discloses several cylindrical wood plugs which are positioned end-to-end and which are impregnated with a salt solution, with a bore being centrally formed in each plug. A pH electrode is positioned in the central bore. Also, a cavity is formed in the end of one of the two end plugs, and a reference electrode is disposed in the cavity. Wood dowel pins connect each plug with the immediately adjacent plugs, and successive dowel pins are longitudinally offset from each other. This provides an interlocking, multi-piece, nonintegral plug which serves as a salt bridge.

In accordance with the Barben invention, each end surface of each piece of the plug which abuts the end surface of another piece is coated with a non-porous substance. Consequently, the only way for ion migration to occur through the capillaries of the wood plugs is for the ions to traverse the tortuous path in sequence through a first plug, then through a first dowel pin, then through a second plug, then through a second dowel pin, and so forth. In this way, ion migration is slowed, delaying the ultimate contamination of the reference electrode.

Unfortunately, the Barben device requires the forming and assembly of several plugs and dowels. This is relatively labor intensive and thus costly. Further, after fabrication of the plug, impregnation with the electrolyte solution is difficult and time consuming.

Accordingly, it is an object of the present invention to provide a pH sensor which permits a low impedance electrochemical connection between the reference cell of the sensor and a specimen fluid. Another object of the present invention is to provide a pH sensor which to a much greater degree retards flow of contaminating ions through the salt bridge to the reference electrode by immobilizing the ions in ion traps. This, in turn, significantly prolongs the service life of the sensor. A further object of the present invention is to provide a pH sensor which is easy to manufacture.

SUMMARY

A pH sensor in accordance with the present invention includes a single integral, i.e., unitary, elongated plug made of semi-permeable material, preferably wood, which is impregnated with an electrolyte, such as a salt, e.g., potassium chloride (KCl). The plug may have a central bore that forms a chamber for holding the pH electrode of a pH electrode sensor. The pH electrode, for example, is a glass tube that is filled with an electrolyte and formed with a pH sensitive glass bulb on the sensing end of the electrode. This bulb protrudes from a first end of the cylindrical plug to contact a specimen fluid. Also, a reference electrode is provided at the second end of the plug in electrochemical contact with that second end. Accordingly, the KCl-impregnated porous plug establishes a "salt bridge" between the reference electrode, near the second end of the plug, and the specimen fluid, with which the first end of the plug is adapted to make contact. Stated differently, electrochemical contact between the reference electrode and the specimen fluid is established by the salt-impregnated porous plug.

As envisioned by the present invention, the plug is a single, unitary piece of material, such as wood. It is preferably cylindrical. When wood is used, the grain of the wood preferably runs in the direction of the axis of the plug. The plug includes several notches which separate the plug into axially spaced traversal zones, and each notch is cut or otherwise formed radially part way through the plug, preferably at an oblique angle relative to the axis of the plug to create dead end ion trap zones. A first portion of each notch extends radially inwardly from the surface of a first side of the plug to the central bore. Moreover, a second portion of each notch extends radially outwardly in the same plane as the first portion from the central bore into the plug, but does not extend to the side of the plug surface which is opposite the first side.

Further, each notch is filled with an impermeable material, preferably epoxy, to prevent ionic communication across the notch. Ionic communication is permitted, however, through each of a plurality of transition zones which are established by those portions of the plug that are radially adjacent to the notches.

As intended by the present invention, the notches are positioned such that successive traversal zones and ion trap zones are on alternating sides of the axis of the plug. Consequently, a major proportion of the ions attempting to traverse the plug end-to-end will be guided by the capillaries of the plug into the first ion trap. Those that escape the trap and migrate laterally through the first transition zone are likely to be caught in the second ion trap, and so on. Stated differently, an ion migrating from the specimen fluid to the reference electrode must pass successively through a plurality of dead end trap zones before reaching the next transition zones and traversal zones. A large amount of the ions remain trapped in these ion trap zones and will not migrate further, thus prolonging the life of the reference electrode.

In accordance with one aspect of the invention, there is provided a device for use in connection with measuring pH in a specimen fluid, which comprises a salt bridge comprising an electrolyte-impregnated unitary semi-permeable plug having a first end adapted to contact the specimen liquid, a second end opposite the first end, a longitudinal axis extending between the first end and the second end, and an outer surface radially outward of the longitudinal axis, wherein the plug has at least a first notch and a second notch formed thereon, the notches being axially spaced from each other, the first notch extending radially inwardly from a first side of the surface of the plug, the second notch extending radially inwardly from a second side of the surface of the plug, and an impermeable material deposited in each the notch to substantially fill the notch, such that a portion of the material in the first notch radially overlaps a portion of the material in the second notch. Preferably, each notch is oriented at an oblique angle relative to the axis. In one embodiment, the semi-permeable material is wood impregnated with an electrolyte. Preferably, the impermeable material is epoxy. The device also preferably includes a housing for closely receiving the plug therein. The device can advantageously further include a reference electrode in electrochemical connection with the second end of the plug and physically separated from direct communication with the specimen fluid by the plug. Moreover, the device becomes a complete pH sensor when pH electrode is included in the housing. The reference electrode can advantageously be located in a recess formed in the second end of the plug. The pH electrode may advantageously extend axially through the plug and protrude outwardly from the first end, and the device may further comprise a porous disc attached to the housing adjacent the first end of the plug.

In accordance with another aspect of the present invention, the invention comprises a pH sensor, comprising a reference electrode, a pH electrode, a salt bridge comprising a unitary plug made of semi-permeable material and saturated with an electrolyte, the plug defining a central axial bore for holding the pH electrode therein, the plug having a first end and a second end between which the axial bore extends and having at least first and second notches axially spaced from each other and cutting radially through at least 50% of the cross section of the plug, the first and second notches extending radially inward from opposite sides of the plug, so that together the first and second notches intercept any direct axial capillary path from the first end to the second end, and a first layer made of impermeable material deposited in the first notch and a second layer of impermeable material deposited in the second notch, wherein the first end of the plug and the pH electrode are adapted to contact a specimen fluid to be measured, and the second end of the plug is in electrochemical contact with the reference electrode and serves to separate the reference electrode from the specimen fluid. Again, the notches are preferably oriented at an oblique angle relative to the axis to provide dead end ion traps, although orthogonal notches are also contemplated. The semi-permeable material is preferably wood impregnated with an electrolyte and the impermeable material is preferably epoxy. The device may also include a housing for receiving the plug therein. Preferably, the pH electrode protrudes outwardly from the end of the plug, and the device further comprises a porous disc attached to the housing adjacent the end of the plug.

The invention also includes a method for physically separating a reference electrode from a specimen fluid during measurement of the pH of the fluid, comprising the steps of interposing a salt bridge between the reference electrode and the specimen fluid, wherein the salt bridge is formed of unitary material impregnated with electrolyte and has axially separated first and second ends and axially extending capillary passageways, and inhibiting ion flow through the passageways by providing at least two alternating slots in the salt bridge extending transversely across the capillary passageways from opposite sides of the salt bridge but not all the way through the salt bridge, so that the slots together cut through substantially all of the capillary passageways, wherein a layer of impermeable material is provided in the slots to inhibit ion flow.

Finally, the invention includes a pH electrode, comprising a unitary semi-porous plug impregnated with an electrolyte, the plug having axially separated first and second ends, a pH electrode positioned at the first end and adapted to contact a specimen fluid, a reference electrode positioned at the second end, and a plurality of ion traps disposed in axial sequence in the plug, each the trap extending radially inwardly from the surface of the plug part way across the plug. Preferably, each ion trap extends inwardly from an opposite side of the plug from the next successive ion trap and includes a layer of impermeable material. In a preferred embodiment, the ion traps are oriented at oblique angles relative to the axis of the plug.

BRIEF DESCRIPTION OF THE DRAWINGS

The details of the construction of the present invention, as well as the operation of the present invention, can best be understood in reference to the accompanying drawings, in which like numerals refer to like parts, and in which:

FIG. 1 is a side view of the pH sensor of the present invention;

FIG. 2 is a cross-sectional view of the pH sensor of the present invention, as seen along the line 2—2 in FIG. 1; and FIG. 3 is a cross-sectional view of the pH sensor of the present invention, as seen along the line 3—3 in FIG. 1.

DESCRIPTION OF THE PREFERRED EMBODIMENT

Referring initially to FIG. 1, a pH sensor is shown, generally designated 10. As shown, the sensor 10 includes a housing 12 which is preferably cylindrically shaped. The housing 12 has a first end 14, and the bulb 16 of a conventional pH electrode 18 (such as a pH sensitive glass bulb) protrudes from the first end 14 to contact a specimen fluid (not shown) for measuring the pH of the specimen fluid. The first end 14 of the plug (but not the rest of the plug) is also adapted to contact a specimen fluid.

FIG. 1 also shows that the housing 12 has a second end 20, and that a coupling, such as the threaded coupling 22, can be attached to the second end 20 for engagement with a complementary fitting (not shown) on a pipe, tank, or other vessel that holds the specimen fluid. A coaxial electrical lead 24 is attached to the pH sensor 18 and extends outwardly from the second end 20 for attachment to a suitable device, i.e., a pH meter, which can process the signal generated by the sensor 10 and indicate the pH of the specimen fluid. As shown in FIG. 1, the sensor 10 includes a potting fixture 26 which establishes a seal between the lead 24 and the coupling 22.

Now referring to FIGS. 2 and 3, the details of the sensor 10 can best be seen. FIG. 2 shows that a unitary, i.e., integral, semi-porous plug 28 is disposed in the housing 12 and is closely receivable therein. The plug 28 can be made of any suitable material, such as porous teflon or wood. As shown in FIG. 2, the plug 28 is substantially cylindrical in shape. Preferably, the plug 28 is saturated, i.e., impregnated, with an aqueous electrolyte or an electrolyte saturated polymer such as polyacrylamide. In one presently preferred embodiment, the plug 28 is impregnated with potassium chloride (KCl). FIG. 2 shows that an epoxy resin 29 is disposed between the plug 28 and the housing 12 to hold the plug 28 within the housing 12.

As further shown in FIG. 2, the plug 28 is formed with a central bore 30, and the pH electrode 18 is positioned in the central bore 30. A seal, such as the annular rubber or plastic O-ring 32, is positioned between the plug 28 and the pH electrode 18 to hold the pH electrode 18 in the central bore 30. The pH electrode 18 can be any suitable pH electrode, such as a hollow glass electrode which is filled with an electrolyte solution.

FIG. 2 also shows that the plug 28 has a first end 34 and a second end 36, and an optional cavity 38 may be formed in the plug 28 adjacent the second end 36. As shown, the epoxy resin 29 covers the second end 36, but does not cover the first end 34. Accordingly, the end of the plug 28 defined by the first end 34 is "open" in the sense that fluid can enter the capillaries of the semi-porous plug 28 which terminate at the first end 34.

A reference electrode 40, which can advantageously be a silver (Ag) wire having a silver chloride (AgCl) coating deposited thereon, is provided in electrochemical contact with the second end 36 of the plug 28. The reference electrode 40 is located in a chamber filled with electrolyte solution, which chamber may advantageously be the cavity 38. Alternatively, a separate chamber adjacent to the second 36 of the plug 28 may be provided for the reference electrode 40. Also, an electrical wire 44 is attached to the reference electrode 40 for establishing a pathway for electrical communication between the reference electrode 40 and a pH measurement instrument or meter (not shown).

Accordingly, the skilled artisan will appreciate that the plug 28 holds both the pH electrode 18, whose bulb 16 can be immersed in a specimen fluid, and a reference electrode 40, which is separated from the specimen fluid by the structure of the plug 28 to reduce the migration of contaminating ions from the specimen fluid to the reference electrode 40. Consequently, the contamination of the reference electrode 40 with ions from the specimen fluid is likewise reduced. Importantly, however, electrochemical communication is established through the salt-impregnated plug 28 between the reference electrode 40 and the specimen fluid in which the bulb 16 of the pH electrode 18 is immersed, to complete the electrical circuit of the pH sensor 10.

To further reduce the migration of ions between the reference electrode 40 and the specimen fluid in which the bulb 16 of the pH electrode 18 is immersed, a plurality of notches 46, 48, 50 are formed, e.g., machined, in the plug 28, and each notch 46, 48, 50 is filled with a respective ion-impermeable layer 54, 56, 58. As shown, the notches 46, 48, 50 are axially spaced from each other. The layers 54, 56, 58 can advantageously be made of the same material as the epoxy resin 29, or may be made of other liquid and ion-impermeable material. While the embodiment shown in FIG. 2 has three notches 46, 48, 50, it is to be understood that a greater or lesser number of notches can be used.

Preferably, each notch 46, 48, 50 is oriented at an oblique angle relative to the axis 52 of the plug 28, for purposes to be shortly disclosed. More specifically, each notch 46, 48, 50 has a first portion adjacent the surface 53 of the plug 28 and an opposite second portion which extends radially into the plug 28, and the second portion of each notch 46, 48, 50 is closer to the first end 34 of the plug 28 than is the first portion of the respective notch 46, 48, 50. For example, the second portion 46a of the notch 46 is closer to the first end 34 than is the first portion 46b of the notch 46. Further, the second portion of each notch radially overlaps the second portion of the axially adjacent notches. For example, the second portion of the notch 48 radially overlaps the second portions of the notches 46, 50. In other words, the notches 46, 48, 50 extend radially inwardly preferably up to the axis of the plug 28 and more preferably at least a minor distance past the axis. The notches 46, 48, 50 can thus extend about 40% or 50% of the diameter of the plug, but preferably extend across about 60% or 70% of the diameter of the plug.

When the notches 46, 48, 50 are formed at an oblique angle, capillaries running in the axial direction from the first end are interrupted by the notches. The oblique angle of the notches 46, 48, 50 not only prevents further axial migration of ions through the capillaries, it also creates a barrier against lateral migration. Thus, the angled notches 46, 48, 50 create ion traps to greatly retard diffusion of contaminating ions from the specimen fluid to the reference electrode.

In accordance with the disclosure above, the notches 46, 48, 50 establish a plurality of transition zones, dead end ion trap zones, and traversal zones on the unitary plug 28. The traversal zones are zones where ions can migrate in the axial direction, or in the direction of the capillaries where the plug 28 is wood. The transition zones are where ions must move laterally or radially into another traversal zone. The ion trap zones are against the angled notches. It is to be borne in mind that while it is convenient to describe the plug 28 in terms of these zones, the plug 28 is nevertheless a unitary piece of electrolyte-impregnated semi-porous material which accordingly establishes electrochemical conductivity between its first end 34 and the reference electrode 40.

More particularly, first and second traversal zones 60, 62 are established on opposite sides of the notch 46. Also, a third traversal zone 64 and a fourth traversal zone 66 are established on opposite sides of the notch 50, and the notch 48 separates the second and third traversal zones 62, 64. A first dead end ion trap zone 61 is adjacent the bottom of the notch 46, a second ion trap zone 63 is adjacent the bottom of the notch 48, and a third ion trap zone 65 is adjacent the bottom of the notch 50.

Connecting serially adjacent traversal zones 60, 62, 64, 66 are first, second, and third transition zones 68, 70, 72. As shown, each transition zone 68, 70, 72 is essentially that portion of the plug 28 that is radially adjacent to the second portion of the respective notches 46, 48, 50. For example, referring briefly to FIG. 3, the first transition zone 68, which connects the first and second traversal zones 60, 62 (shown in FIG. 2), is radially adjacent to the second portion 46b of the notch 46. Importantly, as shown in FIG. 2, the notches 46, 48, 50 are formed in the plug 28 such that successive transition zones 68, 70, 72 are on opposite sides of the axis 52 of the plug 28 from each other.

It may now be appreciated that each notch 46, 48, 50 with impermeable layer 54, 56, 58 establishes an "ion trap" in combination with the structure of the plug 28 described above. Specifically, most of the ions from the specimen fluid which migrate into the end 34 of the plug 28 will be trapped against the impermeable layer 54 within the notch 46 in the first ion trap zone 61. Also, it is believed that most of the ions which migrate from the end 34 through the first traversal zone 60, first transition zone 68, and second traversal zone 62 will be trapped against the impermeable layer 56 disposed within the notch 48 in the ion trap zone 63.

Of the few ions which are able to traverse the tortuous path defined by, in sequence, the first traversal zone 60, first transition zone 68, second traversal zone 62, and second transition zone 70, most will be trapped against the impermeable layer 58 disposed within the notch 50, in the third ion trap zone 65, and so on. Accordingly, while electrochemical contact between the reference electrode 40 and the specimen fluid is established through the plug 28, relatively few ions from the specimen fluid are able to migrate into the reference electrode 40.

FIG. 2 shows that a porous disc 74 is positioned in the first end 14 of the housing 12 to establish a liquid junction between the plug 28 and the specimen fluid. The disc 74 can be any suitable material, e.g., porous Teflon, porous ceramic, or wood. An O-ring 76 is positioned between the epoxy resin 29 and the disc 74 to establish a seal therebetween.

In one method of manufacturing the pH sensor 10, the central bore 30, cavity 38, and notches 46, 48, 50 are machined in the plug 28. Then, the reference electrode 40 is epoxy-bonded to the wall of the cavity 38, and the plug 28 is soaked in a saturated aqueous solution of KCl. The O-ring 32 and pH electrode are then positioned in the central bore 30.

Next, the O-ring 76 and plug 28 are inserted into the housing 12, and the housing 12 is filled with liquid epoxy resin. This epoxy resin hardens into the resin layers 29, 42, 54, 56, and 58. The porous disc 74 is then press fit into the housing 12, and the electrical wire 44 from the reference electrode 40 is soldered to the coaxial shield of the lead 24 from the pH electrode 18. The epoxy potting 26 is then deposited onto the housing 12 to establish a seal between the lead 24 and the housing 12. Alternatively, the wood plug 28 may be impregnated with electrolyte before any of the fabrication steps are undertaken, or may be impregnated after the epoxy resin layers are in place and are cured.

While the reference cell for pH sensor as herein shown and described in detail is fully capable of achieving the objects of the present invention, it is to be understood that no limitations are to be ascribed to the present invention, other than those articulated in the appended claims.

I claim:

1. A device for use in connection with measuring pH in a specimen fluid, which comprises:
   a salt bridge comprising an electrolyte-impregnated unitary semi-permeable plug having a first end adapted to contact the specimen liquid, a second end opposite the first end, a longitudinal axis extending between the first end and the second end, and an outer surface radially outward of the longitudinal axis, wherein said plug has at least a first notch and a second notch formed therein extending part way across the plug, said notches being axially spaced from each other, said first notch extending radially inwardly from a first side of said surface of said plug, said second notch extending radially inwardly from a second side of said surface of said plug; and
   an impermeable material deposited in each said notch to substantially fill said notch, such that a portion of said material in said first notch radially overlaps a portion of said material in said second notch.

2. The device recited in claim 1, wherein each said notch is oriented at an oblique angle relative to said axis to form ion trap zones at said notches to impede the flow of ions through said plug.

3. The device recited in claim 1, wherein said semi-permeable material is wood impregnated with an electrolyte.

4. The device recited in claim 1, wherein said impermeable material is epoxy.

5. The device recited in claim 1, further comprising a housing for closely receiving said plug therein.

6. The device recited in claim 5, further comprising a reference electrode in electrochemical connection with the second end of said plug and physically separated from direct communication with said specimen fluid by said plug.

7. The device recited in claim 6, further comprising a pH electrode in said housing.

8. The device recited in claim 7, wherein said pH electrode extends axially through said plug and protrudes outwardly from said second end, and said device further comprises a porous disc attached to said housing adjacent said second end of said plug and a cavity formed in the second end of the plug in which said reference electrode is located.

9. A pH sensor, comprising:
a reference electrode;
a pH electrode;
a salt bridge comprising a unitary plug made of semipermeable material and saturated with an electrolyte, said plug defining a central axial bore for holding said pH electrode therein, said plug having a first end and a second end between which said axial bore extends and having at least first and second notches axially spaced from each other, said first and second notches extending radially inward from different sides of the plug, so that together the notches intercept an direct axial capillary path from said first end to said second end; and
a first layer made of impermeable material deposited in said first notch and a second layer of impermeable material deposited in said second notch, wherein said first end of said plug and said pH electrode are adapted to contact a specimen fluid to be measured, and said second end of said plug is in electrochemical contact with said reference electrode and serves to separate said reference electrode from said specimen fluid.

10. The device recited in claim 9, wherein each said notch is oriented at an oblique angle relative to said axis to form ion traps for impeding the axial flow of ions through said plug.

11. The device recited in claim 9, wherein said semipermeable material is wood impregnated with an electrolyte.

12. The device recited in claim 9, wherein said impermeable material is epoxy.

13. The device recited in claim 9, further comprising a housing for receiving said plug therein.

14. The device recited in claim 13, wherein said pH electrode protrudes outwardly from said first end, and said device further comprises a porous disc attached to said housing adjacent said first end of said plug.

15. A method for physically separating a reference electrode from a specimen fluid during measurement of the pH of said fluid, comprising the steps of:
interposing a salt bridge between said reference electrode and said specimen fluid, wherein said salt bridge is formed of unitary material impregnated with electrolyte and has axially separated first and second ends and axially extending capillary passageways; and
inhibiting ion flow through said passageways by providing at least two alternating slots in said salt bridge extending transversely across said capillary passageways from different sides of said salt bridge but not all the way through said salt bridge, so that said slots together cut through substantially all of said capillary passageways, wherein a layer of impermeable material is provided in said slots to inhibit ion flow.

16. A pH electrode, comprising:
a unitary semi-porous plug impregnated with an electrolyte, said plug having axially separated first and second ends and functioning as a salt bridge;
a pH electrode positioned at said first end and adapted to contact a specimen fluid;
a reference electrode positioned at said second end; and
a plurality of ion traps disposed in axial sequence in said plug, each said trap extending radially inwardly from the surface of said plug part way across said plug.

17. The pH electrode of claim 16, wherein each said ion trap extends inwardly from a different side of said plug from the next successive ion trap.

18. The pH electrode of claim 17, wherein each said ion trap includes a layer of impermeable material.

19. The pH electrode of claim 18, wherein said ion traps are oriented at oblique angles relative to the axis of said plug.

* * * * *